(12) United States Patent
Sorrentino

(10) Patent No.: US 9,649,181 B2
(45) Date of Patent: May 16, 2017

(54) VIBRATING TOOTHBRUSH

(71) Applicant: COLGATE-PALMOLIVE COMPANY, New York, NY (US)

(72) Inventor: Alan Vincent Sorrentino, Cranbury, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 264 days.

(21) Appl. No.: 14/289,801

(22) Filed: May 29, 2014

(65) Prior Publication Data

US 2014/0259470 A1    Sep. 18, 2014

Related U.S. Application Data

(62) Division of application No. 13/706,282, filed on Dec. 5, 2012, now Pat. No. 8,739,344, which is a division (Continued)

(51) Int. Cl.

| | |
|---|---|
| *A61C 17/22* | (2006.01) |
| *A46B 13/02* | (2006.01) |
| *A61C 17/34* | (2006.01) |
| *A46B 15/00* | (2006.01) |
| *F16F 7/00* | (2006.01) |

(Continued)

(52) U.S. Cl.
CPC ........ *A61C 17/3481* (2013.01); *A46B 13/023* (2013.01); *A46B 15/0002* (2013.01); *A61C 17/22* (2013.01); *A61C 17/225* (2013.01); *F16F 7/00* (2013.01); *A46B 2200/1066* (2013.01); *B26B 19/3866* (2013.01); *H02K 5/24* (2013.01)

(58) Field of Classification Search
CPC .... A46B 13/023; A61C 17/3481; H02K 5/24; H02K 7/061; H02K 7/063; A61H 13/00; A61H 23/0263; B26B 19/28; B26B 19/38; B26B 19/3653; B26B 19/3866; B26B 21/40; B26B 21/52; B26B 21/526
USPC .......... 15/22.1; 132/322; 433/117, 118, 131; 601/142, 70, 72; 310/50, 51, 80, 81; 30/43.5–44, 47–51
See application file for complete search history.

(56) References Cited

U.S. PATENT DOCUMENTS 5,046,249 A * 9/1991 Kawara ................... B26B 21/38
30/44
5,987,681 A    11/1999 Hahn et al.
(Continued)

FOREIGN PATENT DOCUMENTS

BR    0314590-5    8/2005
JP    3-155893    * 7/1991
(Continued)

*Primary Examiner* — Mark Spisich

(57) ABSTRACT

A vibrating toothbrush is provided with vibration-isolating zones that substantially isolate vibrations in the head and reduce vibrations transmitted to the handle without sacrificing structural integrity around the vibration-isolation zones. Such zones may generally comprise neck material that is reduced in cross-section, thinned, replaced by dampening material, or removed altogether to create transmission-inhibiting voids. The vibration-isolating zones may be further supported by the housing of the vibratory element to maintain the structural integrity around the zones and to thereby alleviating weakness conditions that might subject the toothbrush to fatigue and breakage conditions.

18 Claims, 5 Drawing Sheets

Related U.S. Application Data of application No. 13/004,565, filed on Jan. 11, 2011, now Pat. No. 8,327,489, which is a division of application No. 11/460,158, filed on Jul. 26, 2006, now Pat. No. 7,886,393.

(60) Provisional application No. 60/702,474, filed on Jul. 26, 2005.

(51) Int. Cl.
*B26B 19/38* (2006.01)
*H02K 5/24* (2006.01)

(56) References Cited

U.S. PATENT DOCUMENTS

| | | |
|---|---|---|
| 6,421,865 B1 | 7/2002 | McDougall |
| 6,421,866 B1 | 7/2002 | McDougall |
| 6,802,097 B2 | 10/2004 | Hafliger et al. |
| 2002/0120991 A1 | 9/2002 | Cacka et al. |
| 2002/0124333 A1 | 9/2002 | Hafliger et al. |
| 2004/0060138 A1 | 4/2004 | Pfenniger et al. |
| 2005/0011026 A1 | 1/2005 | Hafliger et al. |
| 2005/0108838 A1 | 5/2005 | Schaefer et al. |

FOREIGN PATENT DOCUMENTS

| | | |
|---|---|---|
| JP | 3-261407 | 11/1991 |
| JP | 8-117258 | * 5/1996 |
| JP | 8-126786 | 5/1996 |
| RU | 2174381 | 10/2001 |
| WO | WO 03/037210 | 5/2003 |

* cited by examiner

VIBRATING TOOTHBRUSH

CROSS-REFERENCE TO RELATED APPLICATIONS

This application is a divisional application of U.S. patent application Ser. No. 13/706,282, filed on Dec. 5, 2012, now U.S. Pat. No. 8,739,344, which is a divisional application of U.S. patent application Ser. No. 13/004,565 filed on Jan. 11, 2011, now U.S. Pat. No. 8,327,489, which is a divisional application of U.S. patent application Ser. No. 11/460,158 filed on Jul. 26, 2006, now U.S. Pat. No. 7,886,393, which claims the benefit of priority of U.S. patent application No. 60/702,474, filed Jul. 26, 2005. The entire contents of each of the foregoing applications are expressly incorporated by reference herein.

FIELD OF THE INVENTION

The present invention relates to a vibrating toothbrush generally, and more particularly to a toothbrush having vibrations that are isolated in the head and having reduced transmissions to the handle.

BACKGROUND OF THE INVENTION

Power toothbrushes generally comprise a power source, a motor and a powered element that is driven by the motor. In one type of power toothbrush, a power toothbrush head is provided with movable cleaning elements that are usually driven laterally, rotationally or in an oscillating manner by a motor located in the handle. The motor generates a vibration that is absorbed directly by the hands of the user. However, such vibration is effectively a byproduct of the motor operation and is usually not intended to enhance the effectiveness of the movable cleaning elements. Instead, the vibration provides a tactile sensation to the user and generally creates a perceived feeling of increased cleaning effectiveness.

Another type of power toothbrush relies primarily on vibrations to produce a cleaning operation. These are normally referred to as "sonic"-type brushes because the vibrations generated to achieve a high cleaning efficacy are generally of a frequency of 20-20,000 Hz that can be perceived by the human ear as a "buzz." However, the combination of this sonic noise and the high-frequency vibration felt on one's teeth create a tactile sensation of highly increased effectiveness. To achieve the greatest cleaning, it is preferable to situate the vibration-generation device as close to the toothbrush head as possible so as to focus the vibratory energy near the site of greatest cleaning, and not along the handle.

In some prior art sonic-type brushes, elastomeric regions are provided between the motor and the handle to dampen the vibrations felt in the handle. However, such regions tend to decrease the structural strength of the neck and create localized weaknesses in the neck material that could subject the toothbrush to breakage or cause the toothbrush to fail cyclic fatigue tests. Dampening regions are also noticed in other vibrating-type toothbrushes near the junction of the neck and the handle, usually in the form of an elastomeric section or sections of varying configurations. However, again, such sections create structural weaknesses at a location that usually receives a significant amount of stress during use.

There is a need, therefore, to provide a vibration-powered toothbrush having cleaning vibrations that are directed toward or isolated in the head region and reduced in the handle region, and that do not create weakened areas that subject the toothbrush to breakage and cyclic fatigue.

BRIEF SUMMARY OF THE INVENTION

A vibrating toothbrush is provided with vibration-isolating zones that substantially isolate vibrations in the head and reduce vibrations transmitted to the handle, without sacrificing structural integrity. Such vibration-isolating zones may generally comprise neck material that is reduced in cross-section, thinned, replaced by elastic or dampening material, or removed altogether to create transmission-inhibiting voids. Such zones may be further supported by the housing of the vibratory element to maintain the structural integrity around the zones.

DETAILED DESCRIPTION OF THE INVENTION

Figure 1:
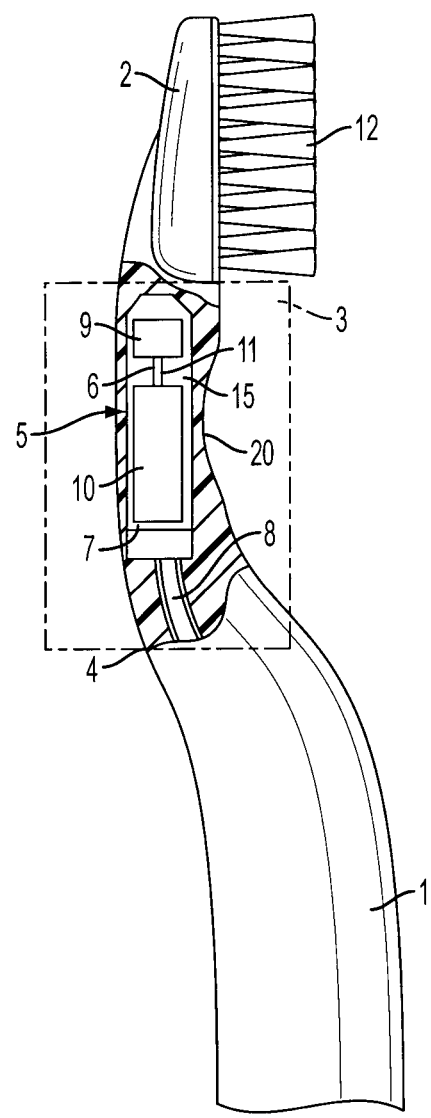
FIG. 1 is a side view of one embodiment of a toothbrush of the present invention.

The vibrating toothbrush of FIGS. 1-4 generally comprises a handle 1, a cleaning head 2 usually having cleaning elements 12, and a neck 3 disposed between the head 2 and the handle 1. While the cleaning head 2 illustrates bristles 12, other cleaning elements of various size, cross-section, material, etc., such as rubber elements, elastomeric elements, polishing elements, abrasive elements, floss-like cleaning elements, etc., may be used. The head 2 and neck 3 are usually formed of a relatively stiff material, such as polypropylene (PP), although other materials may be used. However, such material is also relatively elastic such that the neck and head can vibrate during use.

The neck 3 contains a mechanical vibratory device 5 that preferably includes a motor 10 and a vibratory element such as an eccentric weight 9 connected thereto by a shaft 11. By methods well known in the art, the vibratory device 5 can be connected to a power source such as an electrical power source (e.g., a battery or batteries (not shown)) accommodated in the handle 1 via electrical connections 8 provided in the neck 3, and activated by a switch (not shown). Alternatively, the power source can be located outside of the toothbrush, such as with direct current via a wall socket connection. In addition, the neck 3 can be formed as a unitary structure with the head 2 and handle 1 such as by injection molding or the like, or it can be separable from the handle 1 (not shown) preferably along location 4.

The mechanical vibratory device 5 produces vibrations in the head 2 through rotation of the eccentric weight 9 about the shaft 11. The motor 10 and eccentric weight 9 are preferably accommodated in a structural housing 15, which is preferably positioned in the neck 3 adjacent the head 2. The vibrations produced occur nearest the eccentric weight 9, which is positioned closer to the head 2 than the motor 10, which is closer to the handle 1 than the head 2. As noted above, the neck 3 is preferably made of an elastic material which facilitates the transmission of the vibrations from the weight 9 to the head 2. Of course, the mechanical vibratory device 5 can be positioned in a location that is not adjacent the head 2 as shown, as long as there are means to transmit the generated vibrations to the head 2.

In order to reduce the transmission of vibrations below the eccentric weight 9 or toward the handle 1, the neck construction is altered adjacent or below the eccentric weight 9 to further isolate the vibrations in the head 2. In the embodiment of FIG. 1, the cross-section of the neck 3 is thinned along an exterior section 20 to reduce the amount of neck material below the eccentric weight 9, which in turn reduces the capacity of the neck material to transmit vibrations to the handle 1, and which in turn isolates a majority of the vibrations in the head 2. Structural support for the thinned neck region 20 is provided by the housing 15 of the mechanical vibratory device 5. In other words, the housing 15 reinforces the neck 3 along the thinned region 20. As a result of the thinned neck region 20, a noticeable increase in head vibration is achieved and transmission of vibrations to the handle 1 is minimized, all without sacrificing structural neck strength along the thinned neck region 20. In this embodiment, it is preferable to position the thinned region 20 between the weight 9 and the base 7 of the motor 10, and more preferably along the housing 15, with the motor 10 and/or housing 15 providing structural support for the reduced neck cross section.

Figure 2A:
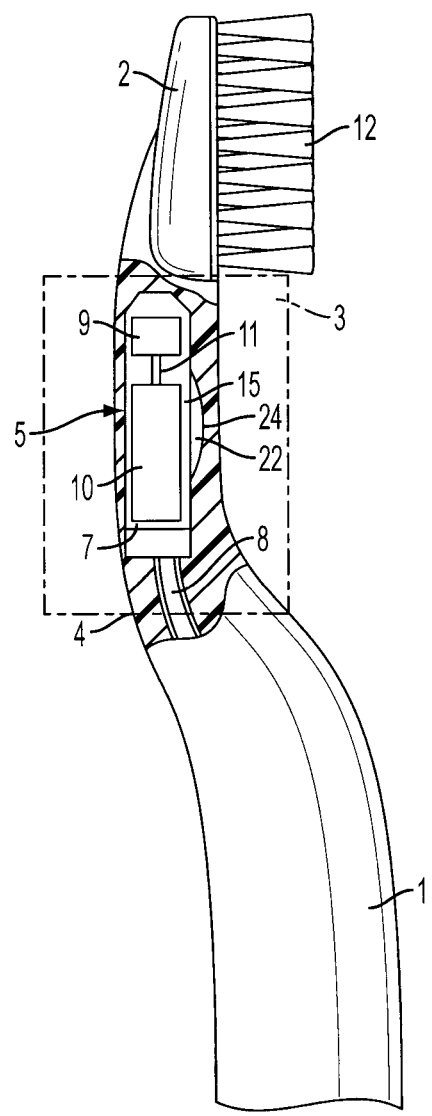
FIGS. 2A and 2B are sides views of alternative embodiments of the invention.

FIG. 2A illustrates an alternative embodiment, wherein material is removed along an interior section 22 of the neck 3 to create one or more void spaces. The interior section 22 would not be visible to the casual observer as the outer neck wall 24 would appear to be uninterrupted. While it is preferred that the interior section 22 exist as a void with the highest vibration dampening capacity, such section may be filled with a dampening material if desired. Again, the mechanical vibratory device 5 and/or housing 15 provide the structural support for the neck 3 around the interior section 22.

Figure 2B:
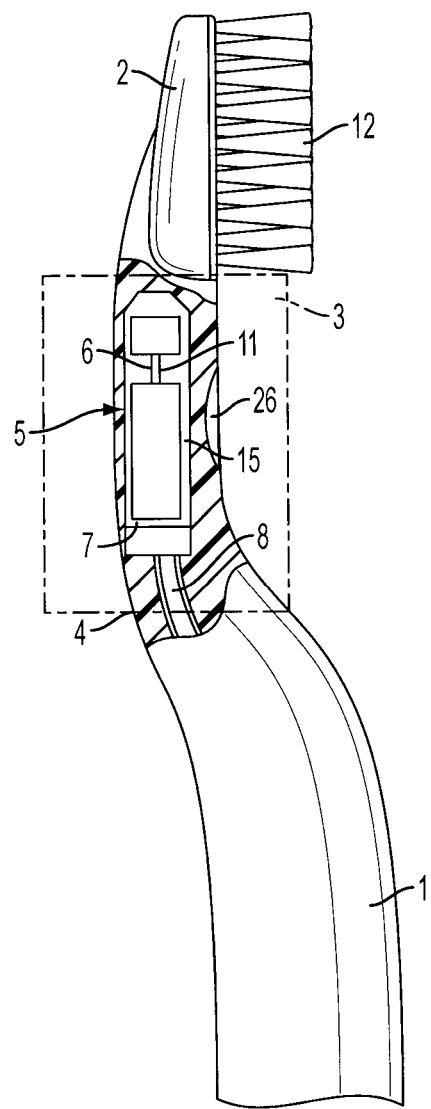

FIG. 2B illustrates an alternative embodiment, wherein neck material is removed along an exterior section 26 of the neck 3 to create one or more void spaces. Such exterior section can extend between the housing 15 and an outer wall of the neck 3. While it is preferred that the exterior section 26 exist as a void with the highest vibration dampening capacity, such section may be filled with a dampening material if desired. In the embodiments of FIGS. 1-2B, the neck, by virtue of the sections 20, 22 or 26, is reduced in cross-section by a magnitude of preferably 5%-90%, and more preferably 10%-50%. This translates into a significant reduction in the transmission of vibrations to the handle, with a significant increase in the isolation of such vibrations in the head.

Figure 3:
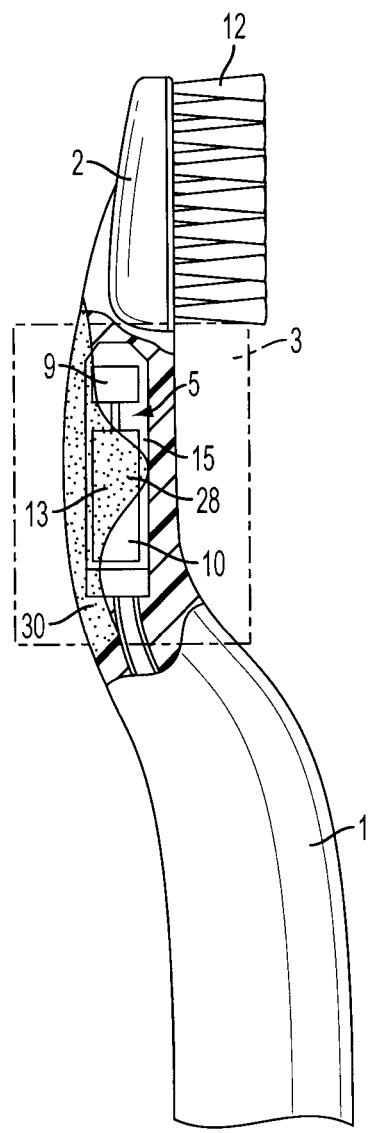
FIG. 3 is a side view of an alternative embodiment of the invention.
Figure 4:
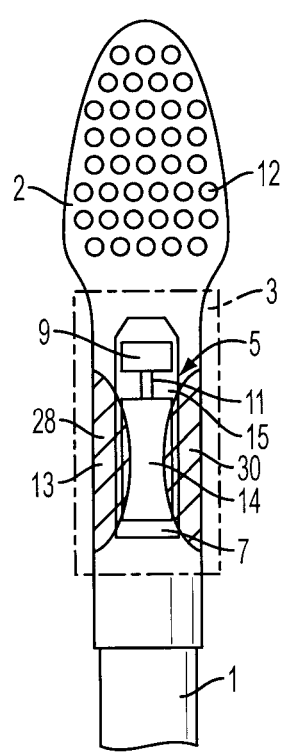
FIG. 4 is a front view of an alternative embodiment of the invention.

In FIGS. 3 and 4, one (FIG. 3) or more (FIG. 4) void regions 28, 30 are created along the sides of the neck 3 and preferably, although not necessarily, filled with dampening material 13. The dampening material 13 has a capacity to transmit vibrations that is less than the transmission capacity of the original neck material. For example, the neck material could be formed from PP, while the one or more void regions, which can be created by strategically removing the PP neck material, can be filled with a thermoplastic elastomer (TPE). Again, the mechanical vibratory device 5 and/or housing 15 provide the structural support for the neck 3 around the void regions 28, 30.

In the embodiment of FIG. 3, for example, the rear of the neck wall can be lined with a dampening material 13 such as TPE along the entire neck region 30, while the sides and front are formed of PP. In such embodiment, the TPE provides a dampening benefit by virtue of its material properties, but its extension beyond the boundaries of the mechanical vibratory device 5 and/or housing 15 do not create a vibration-isolating effect. Instead, additional PP neck portions 28 that are removed and retained as voids or substituted with TPE, act to isolate the vibrations from the device 5 in the head 2, and further reduce the transmission of such vibrations to the handle 1. If filled with TPE, these additional neck portions 28 would preferably constitute forward extensions of the dampening material 13 lining the rear of the neck wall.

In the embodiment of FIG. 4, void regions 28, 30 are provided on both sides of the neck 3 below the weight 9, and are preferably filled with a material 13 having a capacity to transmit vibrations that is less than the capacity to transmit vibrations of the original neck material. A bridge 14 of neck material is defined between the regions 28, 30, to structurally connect head 2 to the handle 1. Again, the mechanical vibratory device 5 and/or housing 15 provide the structural support around the void regions 28, 30.

What is claimed is:

1. A method of isolating vibrations in a head of a toothbrush comprising the steps of:
   a) providing a base of a toothbrush formed of a first material, said base comprising a handle and neck portion of the toothbrush, the base comprising a vibration-reducing section having an exposed outer surface; and
   b) providing a vibration generating device within the base, the vibration generating device having a length;
   wherein the vibration-reducing section of the base is situated along at least a portion of the length of the vibration generating device; and
   wherein the vibration-reducing section comprises a pair of voids formed into the exposed outer surface and arranged on opposing lateral sides of the base.

2. The method in accordance with claim 1, the vibration-generating device being disposed within the neck of the toothbrush.

3. The method in accordance with claim 2, the vibration-generating device being enclosed within a housing, the housing being used to structurally support the vibration-reducing section.

4. The method in accordance with claim 3, wherein the vibration-reducing section is formed by reducing a cross section of the neck.

5. The method in accordance with claim 1, wherein the pair of voids are filled with a dampening material.

6. The method in accordance with claim 5, wherein the dampening material extends through the opposing lateral sides of the base such that the dampening material is in contact with the vibration generating device.

7. The method in accordance with claim 5, wherein the dampening material overlies the portion of the rear surface of the base.

8. The method in accordance with claim 5, wherein a first portion of the vibration-reducing section situated along the portion of the length of the vibration generating device is covered by the dampening material on the opposing lateral sides of the base and a second portion of the vibration-reducing section situated along the portion of the length of the vibration generating device is exposed on the opposing lateral sides of the base.

9. The method in accordance with claim 1, wherein the pair of voids are separated by a bridge connecting a proximal end of the base to a distal end of the base.

10. The method in accordance with claim 9, wherein the bridge is formed on a front surface of the base.

11. The method in accordance with claim 1, wherein the vibration generating device has a distal end proximate the head of the toothbrush, the distal end of the vibration generating device having a perimeter which is entirely surrounded by the base.

12. The method in accordance with claim 1, wherein a front surface of the vibration-reducing section of the base comprises a bridge extending between a proximal end of the base and a distal end of the base, the bridge forming a smooth contoured surface between the proximal and distal ends of the base.

13. A method of isolating vibrations in a head of a toothbrush comprising the steps of:
 a) providing a base of a toothbrush formed of a first material, said base comprising a handle and neck portion of the toothbrush, the base having a vibration-reducing section; and
 b) providing a vibration generating device within the base, the vibration generating device having a length;
 wherein the vibration-reducing section is situated along at least a portion of the length of the vibration generating device; and
 wherein the vibration-reducing section comprises a void on an exposed outer surface of the base, the void formed into a rear surface and opposite lateral sides of the base.

14. The method in accordance with claim 13, wherein the void is filled with a dampening material which surrounds a portion of the rear surface of the base and a portion of the opposite lateral sides of the base.

15. The method in accordance with claim 14, wherein the dampening material covers a portion of the length of the vibration generating device along the opposite lateral sides of the base.

16. The method in accordance with claim 13, wherein a front surface of the vibration-reducing section of the base comprises a bridge extending between a proximal end of the base and a distal end of the base, the bridge forming a smooth contoured surface between the proximal and distal ends of the base.

17. A method of isolating vibrations in a head of a toothbrush comprising the steps of:
 a) providing a base of a toothbrush formed of a first material, the base having a vibration-reducing section; and
 b) providing a vibration generating device within a neck of the base of the toothbrush, the vibration generating device having a length;
 wherein the vibration-reducing section is situated along at least a portion of the length of the vibration generating device;
 wherein the vibration generating device has a distal end proximate the head of the toothbrush, the distal end of the vibration generating device having a perimeter which is entirely surrounded by the base; and
 wherein the vibration-reducing section has a plurality of voids formed into opposing lateral sides of the base, the plurality of voids filled with a dampening material.

18. The method in accordance with claim 17, wherein the plurality of voids extend through the base.

* * * * *